United States Patent
Meng et al.

(10) Patent No.: US 10,428,444 B2
(45) Date of Patent: Oct. 1, 2019

(54) POLYMER NANOFIBERS FROM ELECTROSPINNING OF COMPLEX COACERVATES, AND COMPOSITIONS AND METHODS THEREOF

(71) Applicant: University of Massachusetts, Boston, MA (US)

(72) Inventors: Xiangxi Meng, Sunderland, MA (US); Sarah L. Perry, Belchertown, MA (US); Jessica D. Schiffman, Amherst, MA (US)

(73) Assignee: University of Massachussetts, Boston, MA (US)

( * ) Notice: Subject to any disclaimer, the term of this patent is extended or adjusted under 35 U.S.C. 154(b) by 0 days.

(21) Appl. No.: 15/725,465

(22) Filed: Oct. 5, 2017

(65) Prior Publication Data

US 2018/0100249 A1    Apr. 12, 2018

Related U.S. Application Data

(60) Provisional application No. 62/406,635, filed on Oct. 11, 2016.

(51) Int. Cl.

| | |
|---|---|
| C08L 39/04 | (2006.01) |
| D01F 6/26 | (2006.01) |
| D01D 5/00 | (2006.01) |
| C08F 26/04 | (2006.01) |
| C08F 12/30 | (2006.01) |
| C08F 28/02 | (2006.01) |
| D01F 6/44 | (2006.01) |
| D01F 6/56 | (2006.01) |
| C08L 41/00 | (2006.01) |
| C08L 39/00 | (2006.01) |

(52) U.S. Cl.
CPC ............ D01F 6/26 (2013.01); C08F 12/30 (2013.01); C08F 26/04 (2013.01); C08F 28/02 (2013.01); D01D 5/0038 (2013.01); D01F 6/44 (2013.01); D01F 6/56 (2013.01); *A61L 2400/12* (2013.01); *C08L 39/00* (2013.01); *C08L 41/00* (2013.01); *C08L 2205/16* (2013.01)

(58) Field of Classification Search
CPC ..... D01D 5/003; D01D 5/0038; D01D 5/0046
USPC .................. 264/10, 103, 464, 465, 466, 484
See application file for complete search history.

(56) References Cited

U.S. PATENT DOCUMENTS

| | | | | |
|---|---|---|---|---|
| 2003/0168756 A1* | 9/2003 | Balkus, Jr. | ........... | D01D 5/0038 264/10 |
| 2009/0142505 A1* | 6/2009 | Orr | ........... | D01D 5/0061 427/458 |
| 2010/0041777 A1* | 2/2010 | Schlenoff | ........... | C08J 5/20 521/27 |

FOREIGN PATENT DOCUMENTS

CN        104562438 A  *  4/2015   ............... D01D 5/00

\* cited by examiner

*Primary Examiner* — Leo B Tentoni
(74) *Attorney, Agent, or Firm* — Milstein Zhang & Wu LLC (57) ABSTRACT

The invention provides novel polymer nanofiber or microfiber mats or membranes and methods for their preparation via an aqueous, one-step polyelectrolyte complexation and electrospinning of complex coacervates.

12 Claims, 5 Drawing Sheets

POLYMER NANOFIBERS FROM ELECTROSPINNING OF COMPLEX COACERVATES, AND COMPOSITIONS AND METHODS THEREOF

PRIORITY CLAIMS AND RELATED PATENT APPLICATIONS

This application claims the benefit of priority to U.S. Provisional Application Ser. No. 62/406,635, filed on Oct. 11, 2016, the entire content of which is incorporated herein by reference in its entirety.

STATEMENT REGARDING FEDERALLY FUNDED RESEARCH OR DEVELOPMENT

This invention was made with government support under Grant No. 1727660 by awarded by the National Science Foundation. The Government has certain rights in the invention.

TECHNICAL FIELDS OF THE INVENTION

The invention generally relates to polyelectrolyte complexes and nano-materials and methods for their preparation and use. More particularly, the invention relates to polymer nanofiber or microfiber materials (e.g., mats, membranes) and methods for their preparation via an aqueous one-step polyelectrolyte complexation and electrospinning of complex coacervates.

BACKGROUND OF THE INVENTION

Over the past decade, significant advances have been made in novel drug delivery systems. Polyelectrolyte complexation has been studied as a drug delivery vehicle. Polyelectrolyte complexes (PECs) are associative complexes of one or more predominantly positive polyelectrolytes and one or more predominantly negative polyelectrolytes. They are formed due to a combination of electrostatic and entropic interactions between the oppositely charged polyions. This ion pairing is a type of physical crosslinking, which avoids the use of cross-linking agents (e.g., chemical, physical), thereby reducing the possible toxicity and other undesirable effects of the reagents.

Electrospinning is an established technique used to produce non-woven fiber mats for a variety of applications, such as tissue engineering scaffolds, nanofiltration membranes, and battery materials. Electrospun fiber mats are comprised of randomly accumulated nano- or microscale diameter fibers, which have microscale interstitial spacing, large surface-to-volume ratios, high specific surface area, and interconnected porosity. Although mats have been electrospun from over very diverse types of polymers, green processing has remained a challenge. (Dong, et al. *J. Power Sources* 2011, 196 (11), 4886-4904; Engel, et al. *Materials Today* 2012, 15 (11), 478-485; Deitzel, *J. Polymer* 2001, 42 (19), 8163-8170; Ramakrishna, et al. *Materials Today* 2006, 9 (3), 40-50; Regev, et al. *Polymer* 2010, 51 (12), 2611-2620.)

While the concept of polyelectrolyte complexes as a drug delivery system and other applications have seen heightened interest in recent years, significant obstacles and challenges remain both in processing technologies and functionalities of the resulting materials. A key challenge is the need for a simple, inexpensive and environmentally friendly processing technique.

SUMMARY OF THE INVENTION

The invention provides methods and compositions for a green electrospinning of complex coacervates. The disclosed electrospinning process can be effectively performed in aqueous environment without organic solvent in a one-step process leading to thermally robust and chemically stable fibers.

The invention disclosed herein is the first demonstration that aqueous complex coacervates can be electrospun into chemically robust PEC fiber mats. PECs form as a result of electrostatic complexation between oppositely-charged polymers. The ability of salt to plasticize PECs is utilized to enable the electrospinning of solid fibers. As an example, potassium bromide is used as a plasticizing salt with electrospinning solutions comprise a pair of strong polyelectrolytes, poly(4-styrenesulfonic acid, sodium salt) and poly(diallyldimethyl ammonium chloride). The effect of salt concentration and electrospinning apparatus parameters on fiber formation is shown. Electrospun PEC fiber mats were stable over a wide range of pH values, ionic strength conditions, and many organic solvents.

The invention enables generation of chemically-robust, free-standing PEC fiber mats from electrospinning of aqueous complex coacervates while circumventing the reliance on organic solvents, the challenge of working with entangled polyelectrolytes in solution, and the need to chemically crosslink the as-spun fibers. These PEC fiber mats are especially suited for applications in tissue engineering scaffolds and water purification technologies where environmentally benign fiber mats are imperative.

In one aspect, the invention generally relates to a method for making a nanofiber or microfiber by electrospinning. The method includes: providing an aqueous solution comprising a polyanion and an aqueous solution comprising a polycation; mixing the aqueous solution comprising a polyanion, the aqueous solution comprising a polycation, and an aqueous salt solution to form a coacervate suspension; coalescing the coacervate suspension into a homogeneous coacervate phase; and electrospinning the coacervate phase to form a nanofiber or microfiber.

In another aspect, the invention generally relates to a nanofiber or microfiber prepared by a method disclosed herein.

In yet another aspect, the invention generally relates to a nanofiber or microfiber mat or membrane comprising a nanofiber or microfiber prepared by a method disclosed herein.

In yet another aspect, the invention generally relates to a nanofiber or microfiber mat or membrane constructed according a herein disclosed method.

In yet another aspect, the invention generally relates to a product comprising a nanofiber or microfiber or a nanofiber or microfiber mat or membrane disclosed herein.

BRIEF DESCRIPTION OF THE DRAWINGS

FIG. 1. A schematic overview of the process used to electrospin the coacervate phase to form PEC fiber mats. Photograph shows the electrospinning precursor solution of complex coacervates formed from poly(4-styrenesulfonic acid, sodium salt) (PSS) and poly(diallyldimethyl ammonium chloride) (PDADMAC) in aqueous potassium bromide (KBr). The dense, polymer-rich complex coacervate phase is in equilibrium with the polymer-poor supernatant. A standard single-spinneret electrospinning apparatus was used;

no toxic solvents, chemical crosslinkers, or post-processing is required to form robust PEC fibers.

DETAILED DESCRIPTION OF THE INVENTION

The invention provides a revolutionary approach for making nanofiber or microfiber materials via electrospinning of complex coacervate fibers in a one-step green process that involves an aqueous medium. No organic solvents and/or strongly acidic or basic conditions are required. The invention enables a new platform for fabricating nanofiber materials and for encapsulation.

Much of the difficulty associated with green processing of electrospun mats stems from the poor solubility of most polymers in water. Additionally, empirical evidence suggests that a minimum polymer concentration is required for fiber formation. Neutral polymers form beaded fibers at the entanglement concentration, whereas continuous, bead-free fibers form at ≥2.5 times the entanglement concentration. (Regev, et al. *Polymer* 2010, 51 (12), 2611-2620; McKee, et al. *Macromolecules* 2004, 37 (5), 1760-1767; Schiffman, et al. *Polym. Rev.* 2008, 48 (2), 317-352; Shenoy, et al. *Polymer* 2005, 46 (10), 3372-3384.)

However, the number of neutral, water-soluble polymers is extremely limited. In contrast, the majority of water-soluble polymers are charged polyelectrolytes. Unfortunately, due to the repulsive forces between like charges along the polymer chains, polyelectrolyte solutions in the absence of salt have significantly higher viscosities than neutral polymer solutions prepared at the same polymer concentration. Despite their higher viscosity, polyelectrolyte solutions do not form fibers until 8× the entanglement concentration. While the use of salt to alter precursor solution rheology has been reported, the most common approach for circumventing these incredibly high viscosities is to blend a neutral polymer, such as poly(ethylene oxide) (PEO), into the electrospinning precursor solution. (McKee, et al. *Macromolecules* 2004, 37 (5), 1760-1767; Brenner, et al. *J. Mater. Sci.* 2013, 48 (22), 7805-7811; Spasova, et al. *e-Polymers* 2004, 4 (1), 624-635; Lu, et al. *Polymer* 2006, 47 (23), 8026-8031.)

Adding a neutral polymer can increase the polymer concentration, and thus chain entanglement, without causing a dramatic increase in the solution viscosity. However, nearly all reports on the electrospinning of polyelectrolytes, whether with salt or neutral polymers, still utilize toxic solvents for the spinning process, and often require crosslinking agents to make the mats chemically robust. Solvents and crosslinkers are serious cytotoxicity concerns that have prevented water-soluble polymer-based fiber mats from being widely integrated into advanced materials. (Rieger, et al. *Carbohydr. Polym.* 2016, 139, 131-138; Schiffman, et al. *Biomacromolecules* 2007, 8 (2), 594-601; Brenner, et al. *Carbohydr. Polym.* 2012, 87 (1), 926-929; Zhang, et al. *Polymer* 2006, 47 (8), 2911-2917.)

Investigators have attempted to electrospin mixtures of oppositely charged polymers from a single spinneret; however, electrostatic interactions between the oppositely charged polymers caused the solutions to crosslink in situ, clogging the needle and preventing spinning. To-date all successful reports on electrospinning polyelectrolyte complexes have either used pH to neutralize the charge on one polymer during spinning, toxic solvents that denature the naturally charged polymer, or a challenging dual-spinneret method where two polyelectrolyte/PEO solutions were advanced using a parallel arrangement. (Penchev, et al. *Macromol. Rapid Commun.* 2008, 29 (8), 677-681; Jeong, et al. *Tissue Eng., Part A* 2011, 17 (1-2), 59-70.)

In contrast to the solid PECs typical of layer-by-layer films, complex coacervates are dense, polyelectrolyte-rich liquids that result from the electrostatic complexation of oppositely-charged polymers or other macro-ions in water. Their self-assembly is driven by both electrostatics and entropy, and can be controlled by parameters including the relative concentration of the charged polymers, pH value. (van der Gucht, et al. *J. Colloid Interface Sci.* 2011, 361 (2), 407-422; Perry, et al. *Polymers* 2014, 6 (6), 1756-1772; Priftis, et al. *Macromolecules* 2014, 47 (9), 3076-3085; de Kruif, et al. *Curr. Opin. Colloid Interface Sci.* 2004, 9 (5), 340-349.)

From an application standpoint, the low surface tension of coacervates with water has facilitated the utility of these materials for encapsulation in the food and personal care industries, drug and gene delivery, and as underwater adhesives. However, the liquid nature of complex coacervates has limited their utility in applications where a solid material is required such as, filtration membranes and wound dressings. (van der Gucht, et al. *J. Colloid Interface Sci.* 2011, 361 (2), 407-422; Priftis, et al. *Langmuir* 2012, 28 (45), 15947-15957.)

Polyelectrolytes and macroions, in general, can include water-soluble polymers that are polymerized from charged monomer units, proteins, nanoparticles, and charged surfactant micelles. Individual polyelectrolytes are very challenging to electrospin, typically requiring extreme conditions, such as high voltage, toxic solvents and resulting in fibers that are often unstable after being electrospun.

Complex coacervation is a liquid-liquid phase separation phenomenon resulting from the electrostatic complexation of oppositely charged polyelectrolytes. The resultant coacervate is a dense, polymer-rich liquid retaining both water and salt. Due to their aqueous solubility, polyelectrolyte solutions are a good medium for encapsulating small molecules, such as therapeutic and diagnostic agents.

Fibers fabricated by electrospinning are continuous and have high axial strength and extreme flexibility. Due to the interconnectivity of the fibers, the assembled nanofiber mats have microscale interstitial spaces, large surface-to-volume ratios, and incredibly high porosity. The flexibility and high porosity of nanofiber mats, in conjunction with the beneficial intrinsic effects of increased surface area, make electrospun polymers suited for a variety of application in biomedical, packaging, agricultural, water or air filtration, protective clothing, nanocomposites, and automotive fields.

Electrospun mats thus hold great promise in many fields, including, biomedical, environmental, industrial for example, as vehicle for delivery of drugs and diagnostic agents and as scaffolds for the treatment of chronic wounds and tissue engineering. Additionally, as separation media, functional coatings, and textiles.

Polyelectrolytes and macroions can be classified into various categories. Polyelectrolytes may be natural or synthetic polyelectrolytes. Polyelectrolytes natural and chemically modified biopolymers. Polyelectrolytes may be based on homopolymers and copolymers. Polyelectrolytes can be linear, branched or cross-linked.

Encapsulation of payload into polyelectrolyte complexes may be achieved in multiple ways. For example, the payload can be entrapped from the solution during precipitation of the polyelectrolyte complex. Alternatively, the active drug molecules can be absorbed from the solution and become incorporated into the already formed complex on contact. In another approach, the payload substance may be covalently bound or linked to a complex partner and precipitates during complexation. Furthermore, a component polyion forming the polyelectrolyte complexes may be the active compound itself.

In applications where functioning releases of the payload are desired in select environment or upon designed triggers, the active substance encapsulated in the polyelectrolyte complexes may be released by any suitable means, including by ion exchange mechanism, charge interaction and dissolution of the complex.

The present invention provides polymer nano-/microfiber mats electrospun from a novel class of polymer-rich or macroions liquids, termed complex coacervates, from aqueous solutions and without acid or base solvents. This has been the first demonstration that nanofibers composed of such charged polymer complexes can be electrospun. Complex coacervation can be coupled with electrospinning and salt-driven solidification as a universal, water-only strategy for the encapsulation and delivery of functional molecules such as drugs, proteins, or antimicrobial agents via nanofiber polymer mats.

Among the various parameters for controlling coacervation, an important factor is the charge stoichiometry. The presence of salt can affect coacervation. With zero salt, the coacervate range is narrow and difficult to control. Addition of salt in the complex mixture facilitates coacervate formation due to salt screening effect, which enlarges the coacervate range and reduces strains on processing conditions. Thus, removal of salt can be used effectively to drive solidification.

The as-spun fiber mats can serve as vehicles for encapsulation and delivery of various payloads, such as small molecules, dyes, nanoparticles, pharmaceuticals, proteins, diagnostic agents, etc. The fiber materials can be used in a wide range of applications, such as biomedical, packaging, agricultural, remediation, water or air filtration, protective clothing, nanocomposites, and automotive fields.

In one aspect, the invention generally relates to a method for making nanofibers or microfibers by electrospinning. The method includes: providing an aqueous solution comprising a polyanion and an aqueous solution comprising a polycation; mixing the aqueous solution comprising a polyanion, the aqueous solution comprising a polycation, and an aqueous salt solution to form a coacervate suspension; coalescing the coacervate suspension into a homogeneous coacervate phase; and electrospinning the coacervate phase to form a nanofiber or microfiber.

The nanofiber or microfiber may have any suitable diameter. In certain embodiments, the nanofiber or microfiber has a diameter in the range from about 0.150 micrometers to about 32 micrometers (e.g., from about 0.150 micrometers to about 24 micrometers, from about 0.150 micrometers to about 20 micrometers, from about 0.150 micrometers to about 16 micrometers, from about 0.199 micrometers to about 12 micrometers, from about 0.150 micrometers to about 10 micrometers, from about 0.150 micrometers to about 8 micrometers, from about 0.150 micrometers to about 5 micrometers, from about 0.150 micrometers to about 2 micrometers, from about 2 micrometers to about 32 micrometers, from about 5 micrometers to about 32 micrometers, from about 10 micrometers to about 32 micrometers, from about 16 micrometers to about 32 micrometers, from about 20 micrometers to about 32 micrometers, from about 24 micrometers to about 32 micrometers, from about 2 micrometers to about 10 micrometers, from about 5 micrometers to about 15 micrometers).

In certain embodiments, the method further includes: constructing a fabric or mat or membrane from the electrospun nanofiber or microfiber.

In certain embodiments, the mat or membrane of nanofiber or microfiber has a porosity from about 20% to about 90%.

The polycation may be any suitable cationic polymers or macroions, for example, peptides or proteins, polysaccharides, polymers, nanoparticles, or surfactants.

The polyanion may be any suitable anionic polymers or macroions, for example, peptides or proteins, polysaccharides, polymers, nucleic acids, nanoparticles, or surfactants.

In certain embodiments, the polycation comprises poly (diallyldimethyl ammonium). In certain preferred embodiments, the polycation is poly(diallyldimethyl ammonium).

In certain embodiments, the polyanion comprises poly (styrene sulfonate). In certain preferred embodiments, the polyanion is poly(styrene sulfonate).

In certain embodiments, the salt comprises KBr. In certain preferred embodiments, the salt is KBr. Any suitable salts may be employed, such as NaCl, KCl, LiCl, NaBr, KBr, LiBr, NaI, KI, LiI, $Na_2SO_4$, $NaNO_3$, $CaCl_2$, $MgCl_2$, $MgSO_4$, ammonium formate, as well as transition metal salts, lanthanides, and actinides.

In certain preferred embodiments, the polycation is poly (diallyldimethyl ammonium), the polyanion is poly(styrene sulfonate), and the salt is KBr. The charge stoichiometry is about equal between polycation and polyanion. In certain embodiments, the polycation and polyanion are substantially of equal length. In certain embodiments, the polycation and polyanion are substantially of unequal length.

In preferred embodiments of the invention, the coacervate composition comprises no organic solvent. In preferred embodiments of the invention, the preparation of coacervate does not involve the use of any organic solvent.

In certain embodiments, the applied voltage of electrospinning is from about 6 kV to about 20 kV (e.g., from about 6 kV to about 18 kV, from about 6 kV to about 15 kV, from about 6 kV to about 12 kV, from about 6 kV to about 10 kV, from about 8 kV to about 20 kV, from about 10 kV to about 20 kV, from about 12 kV to about 20 kV, from about 15 kV to about 20 kV).

In another aspect, the invention generally relates to a nanofiber or microfiber prepared by a method disclosed herein.

In yet another aspect, the invention generally relates to a nanofiber or microfiber mat or membrane comprising a nanofiber or microfiber prepared by a method disclosed herein.

In yet another aspect, the invention generally relates to a nanofiber or microfiber mat or membrane constructed according a herein disclosed method.

The nanofiber or microfiber mat or membrane may be of any suitable dimensions (size of area or thickness) dependent on the application. For example, the mat of nanofiber or microfiber may have a size of area from about 0.01 $cm^2$ to about 100 $m^2$ (e.g., from about 0.01 $cm^2$ to about 10 $m^2$, from about 0.01 $cm^2$ to about 1 $m^2$, from about 0.01 $cm^2$ to about 0.1 $m^2$, from about 0.01 $cm^2$ to about 0.01 $m^2$, from about 0.01 $cm^2$ to about 10 $cm^2$, from about 0.01 $cm^2$ to about 0.1 $cm^2$, from about 0.1 $cm^2$ to about 100 $m^2$, from about 1 $cm^2$ to about 100 $m^2$, from about 10 $cm^2$ to about 100 $m^2$, from about 100 $cm^2$ to about 100 $m^2$, from about 1 $m^2$ to about 100 $m^2$) and a thickness from about 1 to about 100 μm (e.g., from about 5 to about 100 μm, from about 10 to about 100 μm, from about 20 to about 100 μm, from about 50 to about 100 μm, from about 1 to about 50 μm, from about 1 to about 20 μm, from about 1 to about 10 μm, from about 1 to about 5 μm, from about 1 to about 3 μm).

In certain embodiment, the nanofiber or microfiber mat or membrane has a therapeutic agent encapsulated therein or adsorbed thereto. Any suitable therapeutic agent may be employed, for example, anti-cancer drugs (e.g., doxorubicin, dacarbazine, paclitaxel), and antiseptics and disinfectants (e.g., chlorohexidine, octenidine dihydrochloride).

In certain embodiment, the nanofiber or microfiber mat or membrane has a diagnostic agent encapsulated therein or adsorbed thereto. Any suitable diagnostic agent may be employed, for example, congo red (gastric function), fluorescein sodium (ophthalmic diagnostic aids), and indocyanine green (liver function) and bentiromide (pancreatic function).

The therapeutic or diagnostic agent may be a small molecule, a peptide, protein or enzyme, an aptamer or nucleic acid.

In certain embodiment, the nanofiber or microfiber mat or membrane has a cell or tissue encapsulated therein or adsorbed thereto. Any suitable cells may be employed, for example, mammalian cells, microbial cells or fungus. Any suitable tissue may be employed, for example, cardiac, skin, wound, and lung tissues.

In yet another aspect, the invention generally relates to a product comprising a nanofiber or microfiber or a nanofiber or microfiber mat or membrane disclosed herein.

Any suitable product may be designed and produced that incorporates or is made of the nanofiber or microfiber or mat or membrane disclosed herein, for example, pharmaceutical preparations, medical devices, wound care products, implants, filters, coatings, clothing, sensors, energy materials, environmental remediation adsorbents and delivery vehicles.

Besides the poly(styrene sulfonate) sodium salt and poly (diallyldimethylammonium) chloride system exemplified herein, a number of other polycations and polyanions can be made into fibers via electrospinning (Table 1 and Table 2).

TABLE 1

Exemplary Cationic Macro-ions Examined via Rheological Characterization of Complex Coacervates

| Name | Strong/Weak | Type |
| --- | --- | --- |
| α-Lactalbumin | Weak | Protein |
| β-Lactoglobulin | Weak | Protein |
| Bovine Serum Albumin (BSA) | Weak | Protein |
| Chitosan | Weak | Polysaccharide |
| Gelatin | Weak | Protein |
| Gelatin A | Weak | Protein |
| Gelatin B | Weak | Protein |
| Jeffamine | Weak | Polymer |
| Lactoferrin | Weak | Protein |
| LAF-1 | Weak | Protein |
| mfp1 | Weak | Protein |
| mfp151 | Weak | Protein |
| O-carboxymethyl chitosan | Weak | Polysaccharide |
| Poly(allylamine hydrochloride) | Weak | Polymer |
| Poly(diallyldimethylammonium chloride) | Strong | Polymer |
| Poly(ether) amine (Jeffamine) | Weak | Polymer |
| Poly(ethyleneimine) | Weak | Polymer |
| Poly(N,N-dimethylaminoethyl methacrylate) | Weak | Polymer |
| Wheat Protein | Weak | Protein |
| Whey Protein Isolate | Weak | Protein |

TABLE 2

Exemplary Anionic Macro-ions Examined via Rheological Characterization of Complex Coacervates

| Name | Strong/Weak | Type |
| --- | --- | --- |
| Agar | Strong | Polysaccharide |
| Alginate | Weak | Polysaccharide |
| β-Lactoglobulin | Weak | Protein |
| DNA | Strong | Nucleic Acid |
| Gelatin | Weak | Protein |
| Gelatin A | Weak | Protein |
| Gelatin B | Weak | Protein |
| Gum Arabic | Weak | Polysaccharide |
| Hyaluronic Acid | Weak | Polysaccharide |
| κ-Carrageenan | Strong | Polysaccharide |
| Pectin | Weak | Polysaccharide |
| Poly(acrylic acid) | Weak | Polymer |
| Poly(aspartic acid) | Weak | Polypeptide |
| Poly(glutamic acid) | Weak | Polypeptide |
| Poly(styrene sulfonate) | Strong | Polymer |
| Polyphosphate | Strong | Polymer |
| Pyrophosphate | Strong | Small Molecule |
| RNA | Strong | Nucleic Acid |
| Sodium Dodecylsulfate | Strong | Surfactant |
| Sodium montmorillonite | Weak | Clay Particle |
| Soy Protein | Weak | Protein |
| Tripolyphosphate | Strong | Small Molecule |
| Xantham gum | Weak | Polysaccharide |

It is noted that although the specific example of PSS and PDADMAC disclosed herein was conducted using KBr as the salt, any suitable salts may be employed. These salts include, but are not limited to: NaCl, KCl, LiCl, NaBr, KBr, LiBr, NaI, KI, LiI, $Na_2SO_4$, $NaNO_3$, $CaCl_2$, $MgCl_2$, $MgSO_4$, ammonium formate, as well as transition metal salts, lanthanides, and actinides. A survey of the effects of some of these various salts on coacervation has been reported. (Perry, et al. *Polymers* 2014, 6, 1756-1772.)

In regard to suitable parameters for electrospinning, a number of factors may be explored for a given system to fine-tune the conditions to achieve the desired functionality and optimal performance. For example, in the exemplary system of PSS and PDADMAC, parameters that can be varied include: the applied voltage (e.g., 2 kV to 20 kV), distance from the nozzle to the collector (e.g., 5 cm to 25 cm), flowrate (e.g., 1.5 mL/hr to 2.5 mL/hr), and polymer/salt concentrations (e.g., defined based on the salt concentration, 1.2 M to 2.0 M KBr).

Additional parameters that can be modified or explored include:
  Initial jet radius
  Volumetric charge density
  Distance from nozzle to collector
  Initial elongational viscosity
  Solution relaxation time
  Perturbation frequency
  Solvent vapor pressure
  Vapor diffusivity
  Surface tension
  Solution density
  Flow rate
  Applied voltage
  Collector (geometry, conductivity, etc.)
  Relative humidity
  Polymer/salt concentration
  Polymer charge stoichiometry
  Polymer polydispersity
  Polymer molecular weight
  Solution pH
  Solvent composition
  Buffer strength The ability to electrospin complex coacervates directly from an aqueous solution is a surprising achievement that would not have been anticipated based on previous results from the electrospinning community. The success of the disclosed invention was unexpected because of the physical understanding that sufficient levels of chain entanglement are required for electrospinning. (McKee, et al. *Macromolecules* 2004, 37 (5), 1760-1767.) Based on the molecular weight of the polymers used in the examples and the concentration of polymers in the coacervate phase, one would not have expected to achieve the high levels of entanglement typically required in a successful electrospinning experiment. (Colby, R. H. *Rheol. Acta* 2010, 49 (5), 425-442.)

Herein disclosed is the first demonstration that solid PEC fibers can be electrospun directly from liquid complex coacervates in an aqueous solution. Chemically stable and thermally robust fiber mats can be formed using an extremely broad range of electrospinning apparatus parameters, including low applied voltages and spinneret-to-collector distances. Electrospinning of saloplastic complex coacervate-based materials has tremendous potential as a green processing strategy that can serve as the basis for developing a new class environmentally benign fiber scaffolds for use in applications, such as wound healing, water remediation, catalysis, and food packaging.

Examples

Electrospinning of Coacervates

Figure 1:
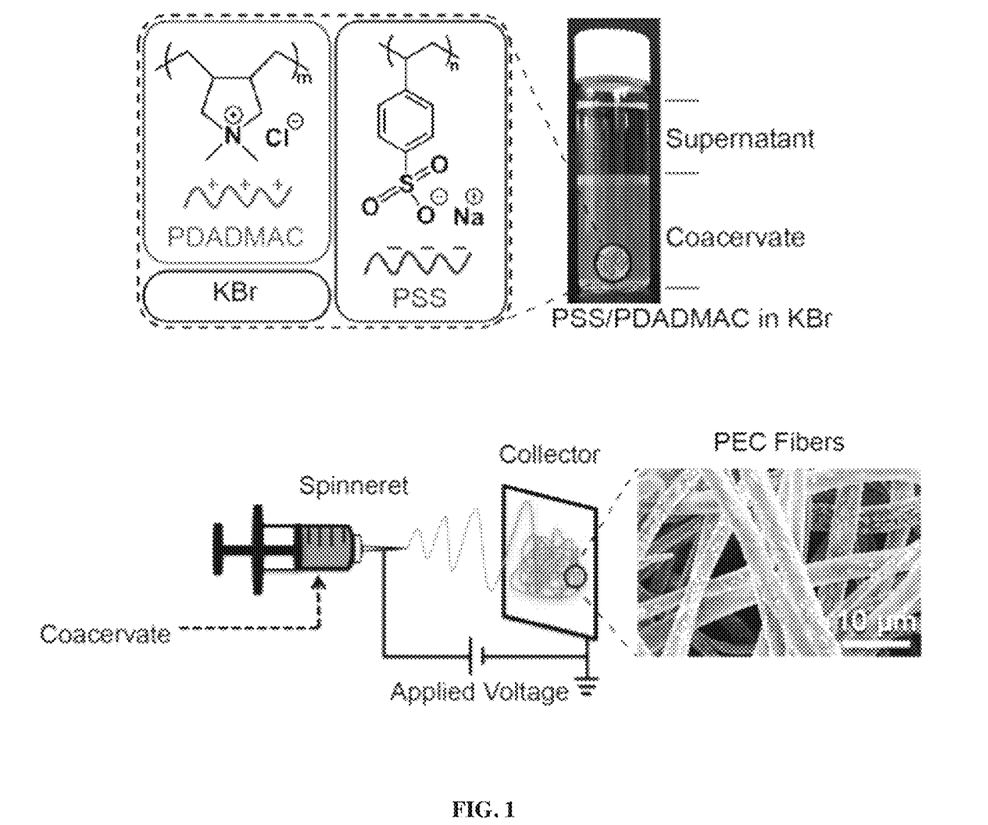

Electrospinning was performed using a traditional single-nozzle spinneret set-up, FIG. 1. The specific coacervates used as the precursor solution were composed of the model saloplastic system, poly(4-styrenesulfonic acid, sodium salt) (PSS) and poly(diallyldimethyl ammonium chloride) (PDADMAC) with potassium bromide (KBr) salt. Coacervates were prepared from bulk solutions at a 1:1 molar ratio of two the strong polyelectrolytes at a total concentration of 0.045M, on a monomer basis.

Figure 2:
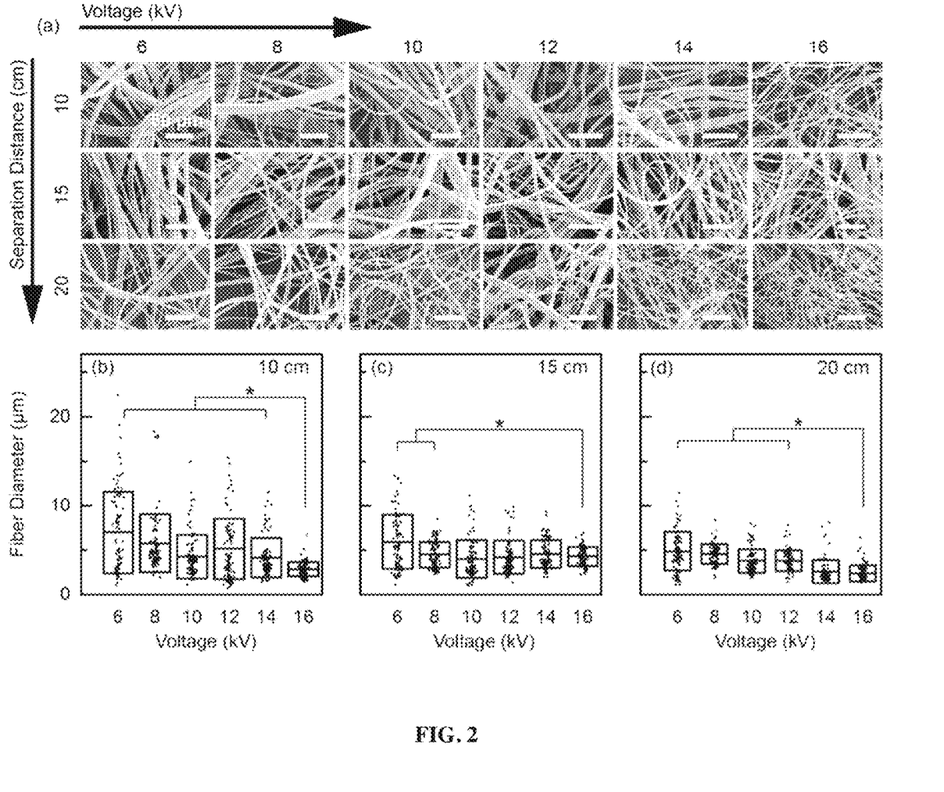
FIG. 2. (a) Scanning electron micrographs (SEM) of PEC fibers electrospun as a function of applied voltage and separation distance. Fiber diameter distribution as a function of applied voltages and spinneret-to-collector distances (b) 10 cm, (c) 15 cm, and (d) 20 cm are displayed in a box plot along with the average fiber diameter (center line) and standard deviation (top and bottom), n=90. An asterisk (*) denotes 95% significance between PEC fibers electrospun using an applied voltage of 16 kV and lower voltages within each figure. All fibers were electrospun from PSS/PDADMAC coacervate in 1.60 M KBr.
Figure 5:
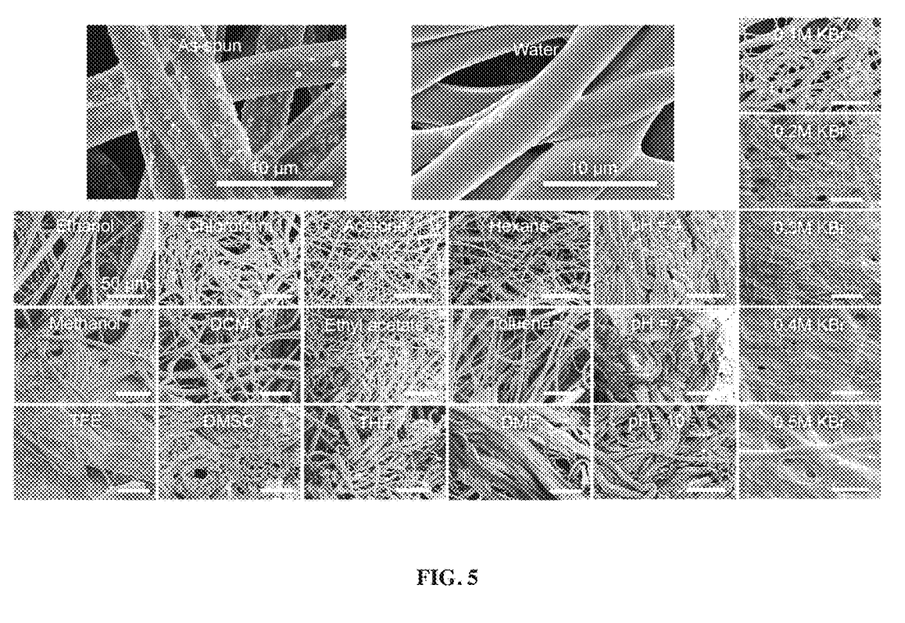
FIG. 5. SEM micrographs comparing as-spun PEC fibers to PEC fibers after rinsing in water, showing the smooth fiber morphology present after the dissolution of KBr crystals. Inset micrographs show PEC fibers after a 60-day immersion in various organic solvents, buffers, and salt solutions. All fibers were electrospun from coacervates in 1.60 M KBr (electrospinning conditions: 16 kV and 20 cm). Scale bars in the inset micrographs are 50 μm.

Continuous, cylindrical PEC fibers were successfully electrospun from an incredibly large range of operating conditions, FIG. 2. The surface of all as-spun PEC fibers was smooth except for the presence of salt crystals, which quickly dissolved after rinsing with water, FIG. 5. Notably, the trends from our systematic investigation into apparatus parameters were consistent with reports from literature.

A decrease in both the average fiber diameter and the distribution of fiber diameters was observed with increasing spinneret-to-collector distance and increasing applied voltage. For example, the PEC fibers electrospun using a spinneret-to-collector distance of 10 cm and an applied voltage of 6 kV had the largest average fiber diameter and greatest size variation (7.0±4.6 μm), while the fibers with the smallest average fiber diameter (2.4±0.8 μm) were electrospun at 20 cm and 16 kV, FIG. 2(*b-d*). The results showed that increased jet whipping/bending time and/or increased electrostatic forces produce thinner fibers.

Figure 3:
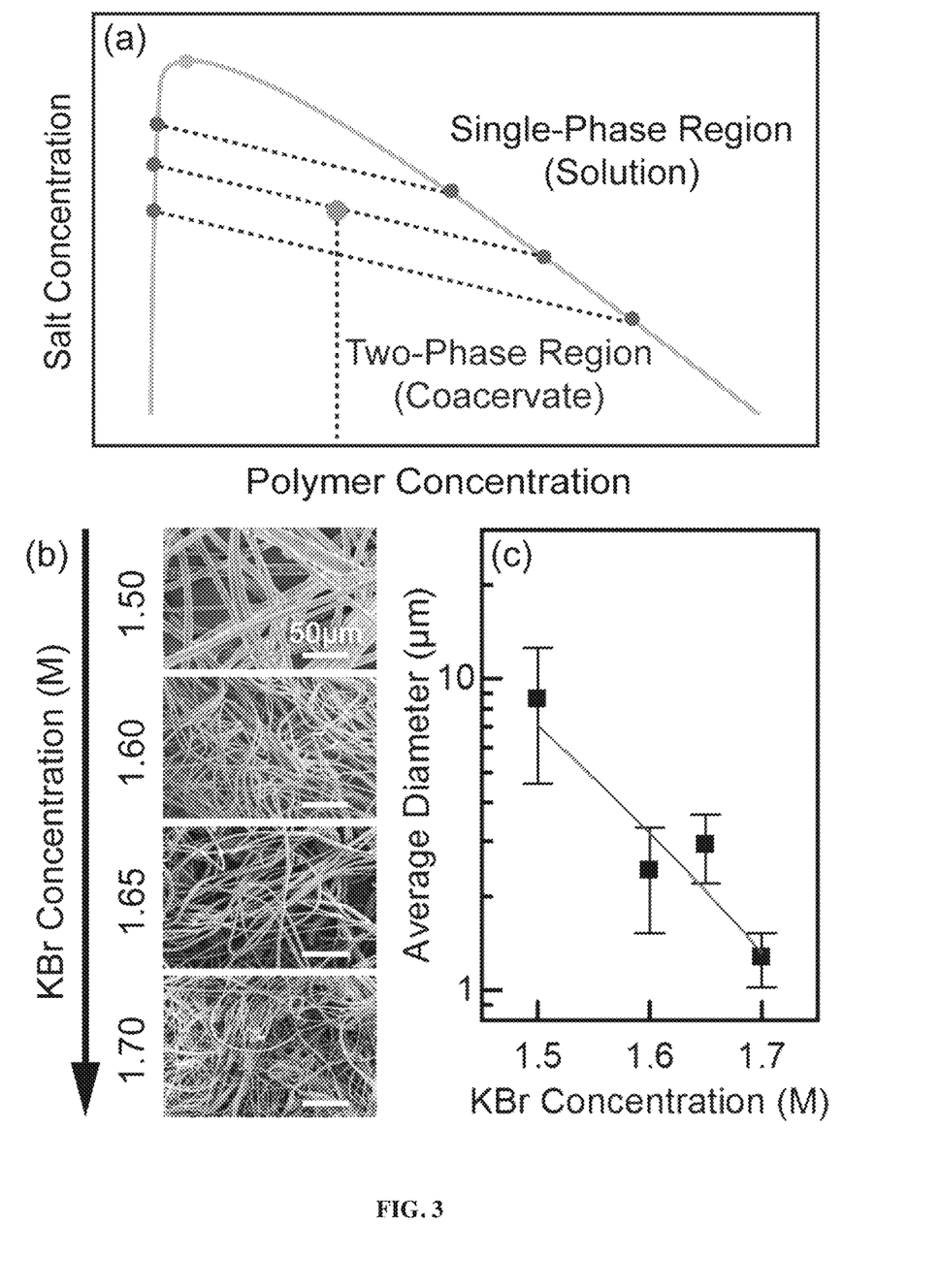
FIG. 3. (a) Schematic representation of the thermodynamic phase diagram, or binodal curve, for complex coacervation, as a function of salt concentration and total polymer concentration (for a given polymer composition, solution conditions, and temperature), defining the boundary between the two-phase region of coacervation (beneath the curve) and the single-phase solution region (above the curve). A sample prepared at a concentration within the two-phase region (blue circle) will phase separate along (dashed) tie-lines to form a polymer-rich coacervate phase and a polymer-poor supernatant phase. (b) SEM micrographs of electrospun fibers as a function of increasing salt concentration (electrospinning conditions: 16 kV and 20 cm). (c) Semi-log plot of average fiber diameter as a function of salt concentration. Error bars indicate one standard deviation, n=90. The line indicates an exponential fit to the data.

Looking beyond apparatus parameters, polymer concentration is one of the most common variables for modulating fiber formation because of the direct relationship between polymer concentration, solution viscosity, and/or the extent of chain entanglement. However, the concentration of polymer in the self-assembled, liquid-liquid phase separated coacervate phase is thermodynamically coupled with salt concentration and cannot be modulated independently, FIG. 3(*a*). A sample prepared at a concentration within the two-phase region will phase separate along tie-lines to form a polymer-poor supernatant and a polymer-rich coacervate phase. Thus, increasing the total polymer concentration present in the initial preparation will not result in a commensurate increase in polymer concentration in the coacervate phase, but will alter the fraction of the resulting mixture which is coacervate vs. supernatant (i.e., the lever rule). Due to the shape of the phase diagram, a more effective strategy for varying the concentration of polymer in the coacervate phase is to vary the salt concentration. An increase in salt concentration within the two-phase region, will result in a decrease in the polymer concentration, and a commensurate decrease in viscosity, FIG. 3(*a*).

The formation of liquid coacervates was observed when the salt concentration was between 1.20 M and 1.75 M KBr. Within this range, of smooth, continuous fibers was successfully electrospun from coacervates formed from 1.50 M to 1.70 M KBr, FIG. 3(*b*). Below 1.50 M KBr, the coacervates were too viscous to extrude through the spinneret, while above 1.70 M KBr the cloudy coacervate was too thin to be centrifuged down or separated from the supernatant for further processing. A plot of fiber diameter as a function of salt concentration shows an exponential decrease in fiber diameter with increasing salt concentration, FIG. 3(*c*), which agrees with previous literature reports describing the relationship between coacervate viscosity and salt concentration.

Figure 4:
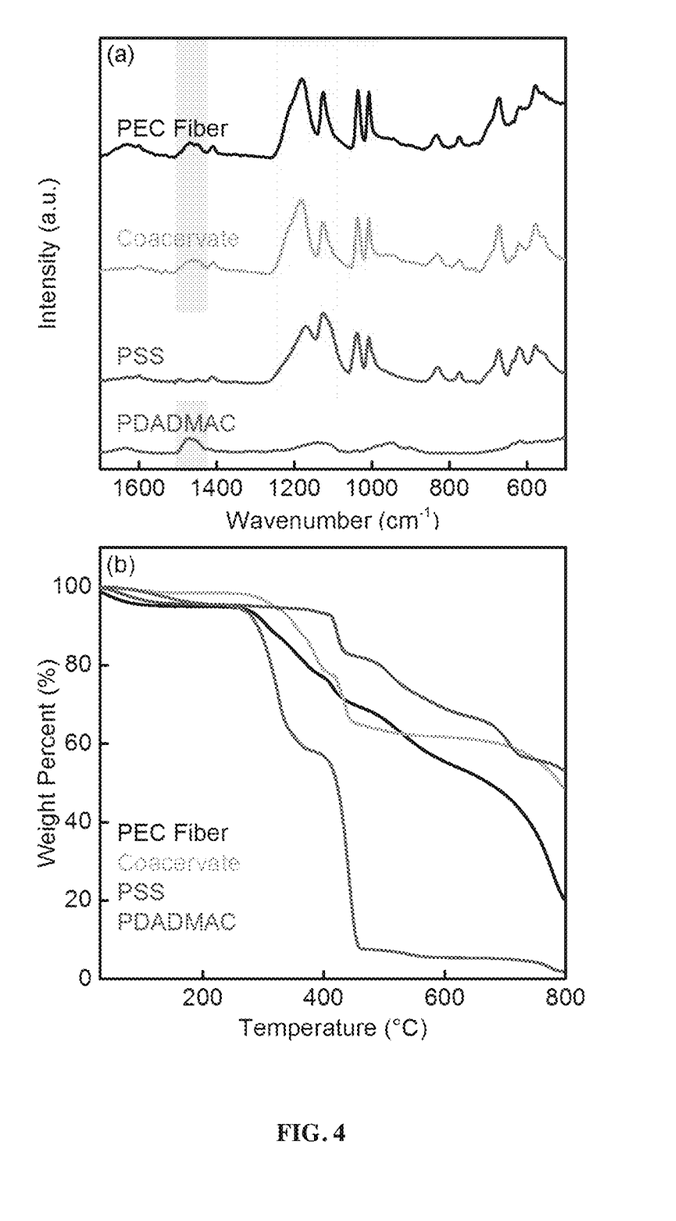
FIG. 4. (a) FTIR and (b) TGA analysis of (black) as-spun PEC fibers prepared from coacervates in 1.60 M KBr (electrospinning conditions: 16 kV and 20 cm), (orange) the lyophilized electrospinning precursor solution of PSS/PDADMAC coacervate in 1.60 M KBr, as well as the lyophilized bulk (blue) PSS and (red) PDADMAC polymers.

Fourier transform infrared (FTIR) spectroscopy was used to confirm the presence of both polymers in the as-spun PEC fibers, FIG. 4(a). The characteristic PSS peaks (highlighted in blue) come from the sulfonic group, which has asymmetric vibrations at 1181 and 1125 $cm^{-1}$ and symmetric vibrations at 1037 and 1008 $cm^{-1}$. The characteristic PDADMAC peak (highlighted in red) is the —C—H bending vibration (1469 $cm^{-1}$). Characteristic peaks for both species are observed in the complex coacervate sample and the resulting electrospun PEC fibers.

Thermogravimetric analysis (TGA) demonstrated the high thermal stability of electrospun PEC fibers, FIG. 4(b), which are a consequence of the electrostatic interactions that drive the self-assembly of the material. As-spun (non-rinsed) PEC fibers displayed a gradual weight loss around 300° C. and it is likely that the remaining mass (~50 wt %) observed at 700° C. is due to residual KBr. The as-spun PEC fibers decomposed at a lower temperature than the lyophilized coacervates, potentially because of their very high surface-to-volume ratio which facilities heat transfer. The bulk polymers, PDADMAC and PSS degraded as expected, releasing methyl chloride and sulfur dioxide as gases, respectively.

A major challenge associated with mats electrospun from water-soluble polymers is the poor stability of the fibers. Rather than relying on chemical crosslinking or other post-processing strategies, the saloplasticity of complex coacervates enables the direct formation of extremely robust fibers. After rinsing the as-spun PEC fibers with water, salt crystals on the surface of the fibers dissolve, FIG. 5. Notably, immersing the PEC fibers in aqueous buffers (pH value=4.0, 7.0, 10.0), aqueous KBr solutions, or a wide range of organic solvents (acetone, chloroform, dichloromethane, dimethylformamide, dimethyl sulfoxide, ethanol, ethyl acetate, hexane, methanol, tetrahydrofuran, and toluene) for 60 days did not dissolve the mats and predominantly showed little impact on fiber morphology, FIG. 5. An exception was the highly fluorinated solvent, 2,2,2-trifluoroethanol, which visually reduced the overall mat porosity, though filament patterns were still visible. Furthermore, the resistance to dissolution by organic solvents was expected from the long history and intractable nature of solid PECs to solvent processing. The stability against pH variation was expected because both PSS and PDADMAC are strong polyelectrolytes. Salt resistance was also consistent with the observed saloplastic behavior of materials formed from PECs. Fibers start fusing together when immersed in KBr solutions above 0.2M, and we observed a significant loss in fiber mat porosity and the crisp distinction between individual fibers above 0.4M KBr.

Materials

Poly(4-styrenesulfonic acid, sodium salt) (PSS, AkzoNobel, VERSA TL130, 15 wt %, ca. 70,000 g/mol, N~340) was filtered using a 0.22 μm pore size filter (EMD Millipore) prior to use. Poly(diallyldimethylammonium chloride) (PDADMAC, Hychem, Hyperfloc CP 626, 20 wt %, ca. 400,000 g/mol, N~2,470), and potassium bromide (KBr, Fisher, ACS grade) were used as received. Deionized (DI) water was obtained from a Barnstead Nanopure Infinity water purification system (Thermo Fisher Scientific, Waltham, Mass.). Organic solvents, including acetone (histological grade), chloroform (ACS grade), dichloromethane (DCM, ACS grade), dimethylformamide (DMF, ACS grade), dimethyl sulfoxide (DMSO, ACS grade), ethanol (ACS grade), ethyl acetate (ACS grade), hexane (ACS grade), methanol (ACS grade), 2,2,2-trifluoroethanol (TFE, ACS grade, TCI America), tetrahydrofuran (THF, ACS grade), and toluene (ACS grade), as well as the aqueous buffer solutions (pH=4.0, 7.0, and 10.0) were utilized as received from Fisher Scientific unless otherwise specified.

Preparation of Complex Coacervates

Individual PSS and PDADMAC stock solutions were prepared gravimetrically at a concentration of 0.25M based on their monomer units, and adjusted to pH 7.2 with a few drops of concentrated HCl or NaOH solutions. KBr stock solution was prepared at a concentration of 2.5M. Complex coacervates were prepared by mixing the KBr solution with water in a centrifuge tube (50 mL, Fisher Scientific), followed by sequential addition of PSS and PDADMAC in a 1:1 molar ratio at a total PEC concentration of 0.045M, on a monomer basis, for all samples. The mixture was vortexed for 15 s immediately after the addition of each solution. Samples were then centrifuged (Sorvall ST 16R Centrifuge, Thermo Fisher Scientific) at 3,500 RPM for 10 min to facilitate coalescence of the dense coacervate phase, FIG. 1.

Electrospinning Procedure

Coacervate samples were loaded into a 5 mL Luer-Lock tip syringe capped with a Precision Glide 20-gauge needle (Becton, Dickinson & Co. Franklin Lakes, N.J.). The syringe was secured to a PHD Ultra syringe pump (Harvard Apparatus, Plymouth Meeting, Pa.). Alligator clips were used to connect the positive anode of a high-voltage supply (Gamma High Voltage Research Inc., Ormond Beach, Fla.) to the needle, while the negative anode to a copper plate wrapped in aluminum foil. For all experiments, the coacervate was fed at a constant rate of 2.5 mL/hr. For experiments testing the effect of salt concentration, an applied voltage of 16 kV and a separation distance of 20 cm were used, along with complex coacervates/solution prepared at 1.20, 1.40, 1.50, 1.60, 1.65, 1.70, 1.75, 1.80 and 2.00 M KBr. To test the effects of the electrospinning apparatus parameters, the KBr concentration was held constant at 1.60 M while applied voltages of 6, 8, 10, 12, 14 and 16 kV and needle-to-collector separation distances of 10, 15, and 20 cm were tested. The electrospinning apparatus was housed in an environmental chamber (CleaTech, Santa Ana, Calif.) maintained at temperature of 23±1° C. and a relative humidity of 25-27% using a desiccant unit (Drierite, Xenia, Ohio). All fiber mats were electrospun for 25 min to achieve a uniform bulk (z-scale) mat thickness.

Characterization of PEC Fiber Mats

Micrographs were acquired using an FEI-Magellan 400 SEM. A Cressington high-resolution ion beam coater model 108 was used to sputter coat samples for 120 s with gold. The distribution of fiber diameters was determined using Image J 1.45 software (National Institutes of Health, Bethesda, Md.) by measuring a total of 90 random fibers from 3 micrographs.

Attenuated total reflectance Fourier transform infrared spectrometer (ATR-FTIR, Platinum ATR, Bruker Alpha) was used to verify the presence of PSS and PDADMAC in the PEC fibers. Lyophilized (Labconco, FreeZone Plus 2.5 Liter Cascade Console Freeze Dry System, Kansas City, Mo.) bulk PSS and PDADMAC polymers, lyophilized PSS/PDADMAC coacervate in 1.6 M KBr, and the corresponding electrospun PEC fibers (applied voltage of 16 kV, spinneret-to-collector distance of 20 cm) were examined.

Thermal gravimetric analysis (TGA, Q50, TA Instruments, New Castle, Del.) was also utilized to characterize the thermal stability of the same four samples described above for ATR-FTIR. All TGA samples were measured in duplicate from 30° C. to 800° C. with a 10° C./min ramp to ensure reproducibility. A clean, dry platinum pan was used to hold the samples for each run. Nitrogen served as balance gas and sample gas.

Stability tests were performed by submerging as-spun PEC fibers in organic solvents (acetone, chloroform, dichloromethane, dimethylformamide, dimethyl sulfoxide, ethanol, ethyl acetate, hexane, methanol, 2,2,2-trifluoroethanol, tetrahydrofuran, and toluene), aqueous buffer solutions (pH=4.0, 7.0, and 10.0), and KBr solutions (0.1, 0.2, 0.3, 0.4, 0.5, 1.0 and 1.8 M) for 60 days. PEC fibers were removed from the solutions and dried before SEM was used to confirm the retention of fibrous morphology.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for making a nanofiber or microfiber by electrospinning, comprising:
   providing an aqueous solution comprising a polyanion or macroanion and an aqueous solution comprising a polycation or macrocation;
   mixing the aqueous solution comprising a polyanion or macroanion, the aqueous solution comprising a polycation or macrocation, and an aqueous salt solution to form a coacervate suspension;
   coalescing the coacervate suspension into a homogeneous coacervate phase; and
   electrospinning the coacervate phase to form a nanofiber or microfiber, wherein the nanofiber or microfiber has a diameter in the range from about 0.199 micrometers to about 32 micrometers.

2. The method of claim 1, further comprising: constructing a mat or membrane from the electrospun nanofiber or microfiber,
   wherein charge stoichiometry of the polyanion or macroanion to the polycation or macrocation is about 1.

3. The method of claim 1, wherein the polycation or macrocation is selected from the group consisting of a peptide or protein, a polysaccharide, a polymer, a nanoparticle, or a charged surfactant molecule or micelle.

4. The method of claim 1, wherein the polyanion or macroanion is selected from the group consisting of a peptide or protein, a polysaccharide, a polymer, a nucleic acid, a nanoparticle, or a charged surfactant molecule or micelle.

5. The method of claim 2, wherein the polycation or macrocation comprises poly(diallyldimethyl ammonium).

6. The method of claim 2, wherein the polyanion or macroanion comprises poly(styrene sulfonate).

7. The method of claim 2, wherein the salt is KBr.

8. The method of claim 2, wherein the polycation or macrocation comprises poly(diallyldimethyl ammonium), the polyanion or macroanion comprises poly(styrene sulfonate), and the salt comprises KBr.

9. The method of claim 8, wherein the salt concentration is in the range from about 1.2 M to about 1.75 M.

10. The method of claim 9, wherein the polycation or macrocation and the polyanion or macroanion are substantially of equal length.

11. The method of claim 9, wherein the coacervate preparation comprises no organic solvent.

12. The method of claim 11, wherein the applied voltage for electrospinning is from about 6 kV to about 20 kV.

* * * * *